United States Patent [19]

Rising et al.

[11] Patent Number: 4,974,462
[45] Date of Patent: * Dec. 4, 1990

[54] FILTER PUNCH AND FILTER COLLECTION SYSTEM

[75] Inventors: Donald B. Rising, Stow; Emile O. Montminy, Lowell, both of Mass.

[73] Assignee: Millipore Corporation, Bedford, Mass.

[*] Notice: The portion of the term of this patent subsequent to Sep. 4, 2006 has been disclaimed.

[21] Appl. No.: 169,523

[22] Filed: Mar. 17, 1988

[51] Int. Cl.$^5$ .............................................. G01N 1/04
[52] U.S. Cl. ............................................... 73/864.041
[58] Field of Search ........... 73/863.23, 864.41, 864.41; 210/85; 55/270; 30/366, 367; 422/68, 89, 101

[56] References Cited

U.S. PATENT DOCUMENTS

| | | | |
|---|---|---|---|
| 2,013,758 | 9/1935 | Livermore | 30/366 |
| 2,145,725 | 1/1939 | Jamieson | 30/366 |
| 4,250,899 | 2/1981 | Pagani | 131/254 |
| 4,277,249 | 7/1981 | Broughton | 435/7 |
| 4,629,236 | 12/1986 | Smith | 294/61 |

Primary Examiner—Robert Raevis
Attorney, Agent, or Firm—Andrew T. Karnakis; Paul J. Cook

[57] ABSTRACT

A filter punch construction is provided for use in conjunction with a multiwell filtration device wherein each well includes a filtration membrane. The punch has a leading flat surface to which is secured an elongated piercing member having a sharp point and a following surface to which is secured a guide member. The piercing member pierces the filtration membrane in each well and the flat leading surface pushes the entire membrane and retentate thereon into a receptacle vial.

10 Claims, 2 Drawing Sheets

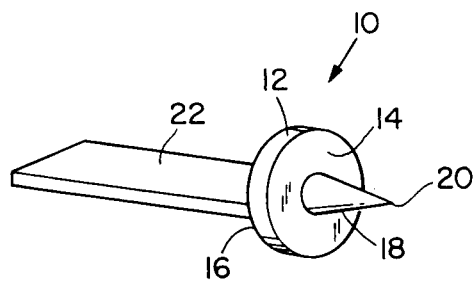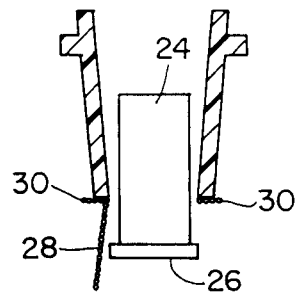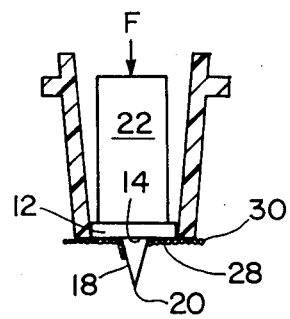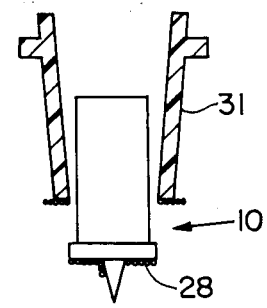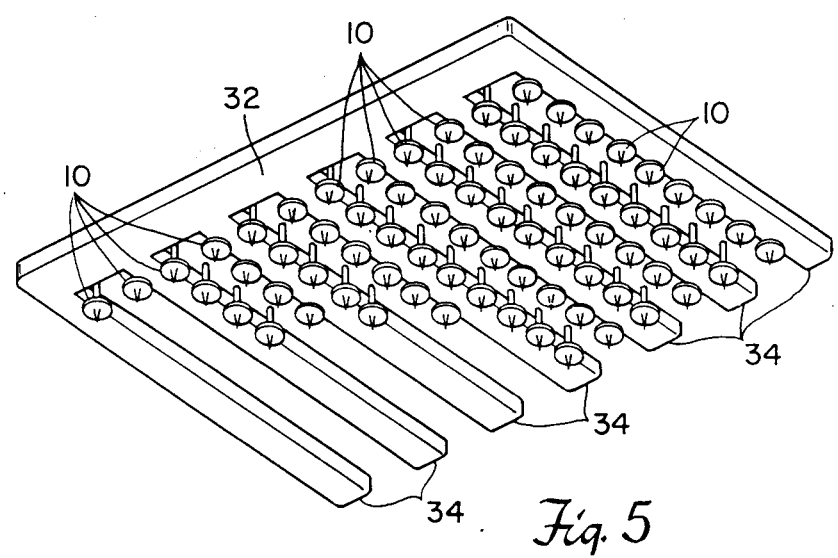
Fig. 1
Fig. 2
PRIOR ART
Fig. 3
Fig. 4
Fig. 5

FILTER PUNCH AND FILTER COLLECTION SYSTEM

BACKGROUND OF THE INVENTION

This invention relates to a filter punch construction and to a system utilizing the filter punch for collecting sample deposited on a filter.

Test plates for in vitro analysis which contain a multiplicity of individual wells or reaction chambers are commonly known laboratory tools. Such devices have been employed for a wide variety of purposes and assays as exemplified by U.S. Pat. Nos. 3,694,464; 4,304,865; 4,276,048; 4,154,795; 4,427,415; 4,526,690 and Re. 30,562. Microporous membrane filters and filtration devices containing such microporous membranes have been especially useful with many of the recently developed cell and tissue culture techniques and assays, particularly those in the field of virology and immunology, wherein the material of interest is retained by the filter. Typically, ninety-six well filtration plate is used to conduct multiple assays simultaneously, some steps of which last several hours prior to performing filtration. Subsequent to filtration, it is common practice to utilize a die-punch having a flat face which is inserted into the well and through the filter paper bearing the retentate in order to direct the filter paper and retentate from the well into a vial for subsequent testing. This system has two major problems. First, many times only a portion of the filter paper circumference is sheared and the filter disc remains attached to the well. Secondly, the flat face of the punch tends to remove some of the retentate from the filter paper so that the subsequent testing is inaccurate. An alternative system utilizes a hollow tube as a punch to minimize the contact face of the punch and reduce the amount of sample accidentally transferred to the punch. In another system, the filter is scored about its circumference in order to facilitate subsequent punching. This system is undesirable since accidental rupturing of the filter paper along the scoring can occur.

Accordingly, it would be desirable to provide a means for removing retentate and filter paper from a multi-well filtration plate which assures that the filter paper will be completely removed from the well without loss of a portion of the retentate for purposes of subsequent testing. Furthermore, it would be desirable to provide such means which permits removal of the filter and retentate from a plurality of wells simultaneously.

SUMMARY OF THE INVENTION

The present invention provides a filter punch and filter punch system which can be utilized in conjunction with a multi-well filtration plate in order to remove retentate and filter from each well subsequent to a filtration step which utilizes the multi-well filtration plate. The filter punch includes an elongated piercing member having a sharp point on a lead surface of the punch and a guide protrusion from a following surface of the punch. The piercing point is positioned to pierce the central portion of the filter in the well while the guide protrusion is positioned to permit a guide to push the punch through the filter paper. The piercing point pierces the central portion of the filter and the flat punch face which follows the piercing point then contacts essentially the entire area of the filter within the well thereby to push the entire filter out of the well and into a receptacle wherein the retentate can be tested. There is no loss of retentate since the filter punch accompanies the filter paper with all of the retentate positioned between the filter paper and the punch face surface. In another aspect of this invention, a filter punch holder is provided for retaining rows of punches in a manner so that a plurality of filter punches can be utilized simultaneously to remove retentate and filter from a plurality of wells.

BRIEF DESCRIPTION OF THE DRAWINGS

FIG. 1 shows a filter punch of this invention.

FIG. 2 illustrates the undesirable operation of one embodiment of the prior art.

FIG. 3 illustrates the first step of the use of the filter punch of this invention.

FIG. 4 illustrates the second step of the use of the filter punch of this invention.

FIG. 5 illustrates the filter punch holder of this invention.

DESCRIPTION OF SPECIFIC EMBODIMENTS

Figure 6:
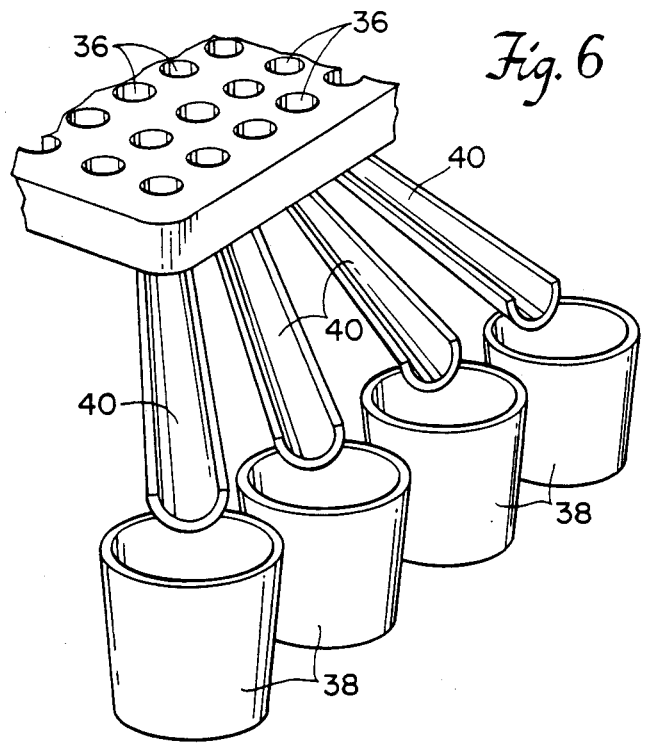
FIG. 6 illustrates the use of the filter punch and filter punch holder of this invention.

Referring to FIG. 1, the filter punch 10 includes a punch section 12 having two opposing flat surfaces 14 and 16. On flat surface 14, a conically shaped filter piercing member 18 is secured thereto. The conically shaped piercing member 18 has a sharp point 20 adapted to pierce filter membrane. On the surface 16 a die-punch guide 22 is secured which functions to position a hollow die about the circumference of punch section 12 so that even distribution of force across the punch section 12 can be applied. The guide member 22 can be of any shape such as shown in FIG. 1, cylindrical, hollow cylindrical or cruciform. The sides of the filter piercing member 18 form an angle with the vertical axis of the piercing member of between about 2° and about 45°, preferably between about 5° and about 30° and have a length generally between about 0.2 mm and about 10 mm, preferably between about 1 mm and about 3 mm.

Referring to FIG. 2, the filter punch 24 of the prior art has a flat face 26 which is designed to sever filter section 28 from the remaining portion of the filter 30 so that it will be directed to a receptacle (not shown). However, the flat face 26 frequently causes incomplete severance so that the filter section 28 remains hinged on to filter section 30 rather than dropping into the desired receptacle.

Referring to FIG. 3, the filter punch of this invention is utilized so that a force (F) is applied to guide section 22 so that point 20 of conically shaped piercing member 18 is pushed through filter 28 and then flat surface 14 of section 12 removes filter section 28. As shown on FIG.

4, the filter punch 10 and filter section 28 are passed from well 31 into a receptacle (not shown).

Referring to FIG. 5, a filter punch holder of this invention is shown which includes a base member 32 and a plurality of arms 34 which are attached to the base member 32 and extend substantially parallel to each other. A plurality of filter punches 10 as shown in FIG. 1 are secured along the length of each of the arms 34 substantially equidistant from each other as shown in FIG. 5. The distance between the punches 10 is such as to accomodate the distance between the wells 36 in the multiwell filtration apparatus (FIG. 6). The punches 10 can be secured to the arms 34 by any means. However, it is preferred that the base 32, arms 4 and filter punches 10 be molded as one piece in order to facilitate placement of as many as 96 punches 10 over the corresponding wells 36. The filter punch holder shown in FIG. 5 is utilized in conjunction with multiple plungers which are positioned to parallel the rows of filter punches 10 shown in FIG. 5. The filter punches 10 are positioned above wells 36 and pass through the filter in the manner shown in FIGS. 3 and 4 to sever the filter from the wells 36 whereby individual filter punches 10 and filter sections 28 pass into vials 38 by means of chutes 40. Each punch 10 adds enough mass to each filter section 28 to cause the combination to slide down a chute 40 while the filter section 28 alone would adhere to the chute 40.

Figure 7:
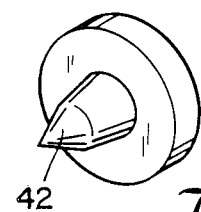
FIG. 7 illustrates an alternative embodiment of this invention.
Figure 8:
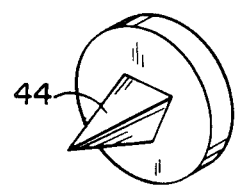
FIG. 8 illustrates an alternative embodiment of this invention.
Figure 9:
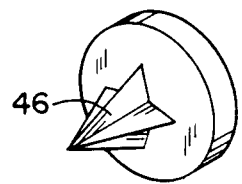
FIG. 9 illustrates an alternative embodiment of this invention.
Figure 10:
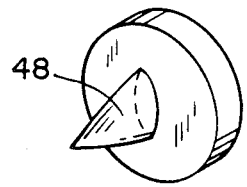
FIG. 10 illustrates an alternative embodiment of this invention.
Figure 11:
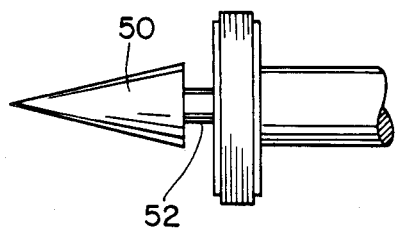
FIG. 11 illustrates an alternative embodiment of this invention.

The filter punch construction of this invention as exemplified by FIGS. 1,7,8,9,10 and 11 are made so that the centrally located piercing member, during use stabilizes the membrane during punching so that it is severed about its entire periphery. The piercing member provides an anchor point to hold the punched member and has a point which is sufficiently sharp to pierce the membrane before the membrane begins to separate from the well by shearing or seal failure. The sides of the piercing member should form a small angle with its vertical side so that the piercing member can penetrate the membrane easily. By forming the sides of the piercing member so that they form a small angle with the vertical axis, the pierced membrane will more easily grip the piercing member. As shown in FIG. 7, the piercing member 42 can be formed as a double cone. The piercing member 44 shown in FIG. 8 is in the form of a pyramid. The piercing member 46 shown in FIG. 9 has a cruciform shape. The piercing member 48 shown in FIG. 10 has a stiletto shape. The piercing member 50 shown in FIG. 11 has an undercut 52 so that it functions as a barb. As shown in FIG. 11, the undercut 52 has a smaller cross section then the base of piercing member 50. The piercing member also can be formed so that it has a short conical piercing head attached in a cylindrical member which in turn, is secured to a surface of the punch section.

Figure 12:
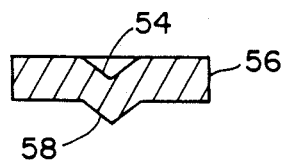
FIG. 12 is a cross-sectional view of a filter punch of this invention having a depressed guide means.

As shown in FIG. 12 the guide member 54 is in the form of a conical depression which mates with a punch (not shown) to stabilize and effect the desired force on the punch 50 having piercing member 58 of this invention. Thus, the guide member utilized in the present invention may either be an extension or depression relative to the punch section.

Although several embodiments of the invention have been described in detail above, modifications will become apparent to those of skill in the art. Accordingly, the invention is intended to be limited only by the appended claims.

We claim:

1. A filter punch which comprises a punch section having a thickness and two opposing surfaces,
    a filter piercing member secured to an extending from one of said opposing surfaces, said one of said opposing surfaces comprising a flat surface, said filter piercing member having a sharp point and having a side area and a vertical axis, said side area and said vertical axis forming a small angle such that a filter pierced by said piercing member is secured to said piercing member and
    a punch guide comprising an extension formed on the second of said opposing surfaces, said punch section, piercing member and guiding having a size and shape to permit said filter punch to pass through a filter having substantially the same size and shape of said one of said opposing surfaces.

2. The filter punch of claim 1 wherein said filter piercing member is conically shaped.

3. The filter punch of anyone of claims 1 or 2 wherein said piercing member has a conical angle between about 5° or 30°.

4. The filter punch of claim 1 wherein said filter piercing member is secured to one of said opposing surfaces by means of a cylindrical member.

5. The filter punch of claim 4 wherein said cylindrical member has a cross-section smaller than a base of said filter piercing member.

6. The filter punch of claim 1 wherein said punch is used to convey said filter to a receiving means.

7. A filter punch holder which comprises; a base member,
    a plurality of arms attached to said base member, said arms being positioned substantially parallel to each other,
    each of said arms having a plurality of filter punches secured along the length of said arms, said filter punches being positioned substantially equidistant from each other,
    each of said filter punches comprising a punch section having a thickness two opposing surfaces and a filter piercing member secured to an extending from one of said opposing surfaces, said one of said opposing surfaces comprising a flat surface, said filter piercing member having a sharp point and having a side area and a vertical axis, said side area, and said vertical axis forming a small angle such that a filter pierced by said piercing member is secured to said piercing member
    and a punch guide comprising an extension formed on the second of said opposing surfaces,
    said punch section, piercing member and punch guide having a size and shape to permit said filter punches to pass through a filter having substantially the same size and shape of said one of said opposing surfaces.

8. The filter punch holder of claim 7 which is formed of unitary construction.

9. The filter punch holder of claims 7 wherein said filter piercing member is conically shaped.

10. The filter punch holder of any one of claims 7, 8 or 9 wherein said piercing member has a conical angle between about 5° and 30°.

* * * * *